United States Patent [19]

Guillen

[11] Patent Number: Plant 7,669

[45] Date of Patent: Oct. 8, 1991

[54] NEW GUINEA IMPATIENS PLANT NAMED CELEBRATION HOT PINK

[75] Inventor: Mario A. Guillen, Cartago, Costa Rica

[73] Assignee: Ball Seed Co., West Chicago, Ill.

[21] Appl. No.: 531,547

[22] Filed: Jun. 1, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A distinct New Guinea Impatiens plant named Celebration Hot Pink characterized by its iridescent hot pink flower color, large flowers, upright and vigorous habit, variegated leaves, floriferous habit, and excellent branching.

1 Drawing Sheet

The present invention relates to a new and distinctive cultivar of New Guinea Impatiens plant, botanically known as New Guinea Impatiens and known by the cultivar name Celebration Hot Pink. The new cultivar was developed by me through controlled breeding by crossing presently unknown male and female parents of selections of Pan American Seed, Linda Vista, Costa Rica.

Asexual reproduction by terminal cuttings taken at West Chicago, Ill., has shown that the unique features of this new New Guinea Impatiens are stabilized and are reproduced true to type in successive propagations.

The following characteristics in combination distinguish the new Impatiens from other impatiens cultivars of this type known and used in the floriculture industry.

1. Hot pink and iridescent flower.
2. Upright and vigorous habit.
3. Floriferous habit.
4. Large flowers.
5. Variegated foliage.
6. Excellent branching.
7. Flowers are positioned above the foliage in uniform display.

The new cultivar is similar in flower color to the cultivar Pulsar, disclosed in U.S. Plant Pat. No. 5,783, with which Celebration Hot Pink can be compared. Reference is made to attached Chart A which notes dissimilar characteristics between the respective cultivars. To summarize, compared to Pulsar, Celebration Hot Pink has a more upright and vigorous habit, flowers which are held above the foliage in a uniform display, more freely flowering, more breaks per plant, variegated foliage, and larger flowers.

The accompanying colored photograph illustrates the overall appearance of this cultivar, showing colors as true as it is reasonably possible to obtain in a colored reproduction of this type.

The following is a detailed description of my new New Guinea Impatiens cultivar based on plants produced under commercial practice in West Chicago, Ill., in a glass-covered greenhouse with day temperatures of 24° to 26° C. and night temperatures of 18° to 20° C.

Color references are made to The Royal Horticultural Society Colour Chart except where general terms of ordinary dictionary significance are used.

Propagation:

A. *Type cutting.*—Terminal tip.

B. *Time to initiate roots.*—5 days at 24° C. summer; 7 days at 21° C. winter.

C. *Rooting habit.*—Fibrous, branching.

Plant description:

A. *Form.*—Freely branching, vigorous.

B. *Habit of growth.*—Spreading, upright habit, 22 cm. by 24 cm.; asymmetrical.

C. *Foliage.*—1. Size: 8 to 10 cm in length, 3.5 cm wide. 2. Shape: Ovate, acuminate tip with attenuate base. 3. Texture: Smooth. 4. Margin: Finely serrated. 5. Color: Green with yellow variegation. Young foliage: Top side 139A; under side 137B. Mature foliage: Top side 139A; under side 137C. 6 Variegation: 153C. 7. Venation: 68B.

Flowering description:

A. *Flowering habits.*—Freely flowering.

B. *Natural flowering season.*—Year-round in greenhouse environment.

C. *Flower bud shape and color.*—Conical, 57A.

D. *Flowers borne.*—Above foliage, arising from leaf axils.

E. *Quantity of flowers.*—10 to 12 per branch.

F. *Petals.*—1. Shape: Cordate. 2. Color: Hot pink, iridescent. Top side, 57A when opening, 57B at maturity, fading to 57C. Under side 57C. 3. Number of petals: 5. 4. Size of flowers: 5.5 cm (width)×6 cm (length).

G. *Reproductive organs.*—1. Stamens: 5 in number. a. Anther shape: Oblong. b. Anther color: 10D. c. Pollen color: 11C. 2. Pistils: a. Stigma shape: Round. b. Stigma color: 154D. c. Style color: 143B. d. Ovary number: Superior, 5-celled. e. Ovary size: 1 cm (length). f. Ovary color: 143C.

Disease resistance: No fungal or bacterial problems observed.

CHART A

| Characteristic | Celebration Hot Pink | Pulsar |
|---|---|---|
| Plant height | 10 cm | 6 cm |
| Plant diameter | 22 cm by 24 cm.; asymmetrical | 15–18 cm |
| Branches/plant | 6 | 4 |
| Foliage color Top side | 139A, variegated with 153C | 147A non-variegated |
| Flower color Top side | 57B | 57A |
| Flower size | 5.5 cm × 6 cm | 5 cm × 4.5 cm |

I claim:

1. A new and distinct cultivar of New Guinea Impatiens plant named Celebration Hot Pink, as illustrated and described.

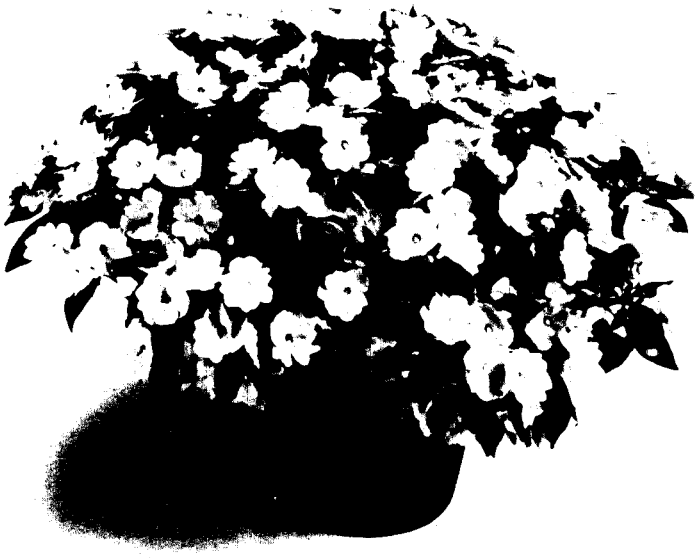

* * * * *